(12) United States Patent
Mills

(10) Patent No.: US 7,015,352 B2
(45) Date of Patent: Mar. 21, 2006

(54) PRO DRUGS FOR SELECTIVE DRUG DELIVERY

(76) Inventor: Randell L. Mills, 493 Old Trenton Rd., Cranbury, NJ (US) 08512

(*) Notice: Subject to any disclaimer, the term of this patent is extended or adjusted under 35 U.S.C. 154(b) by 0 days.

(21) Appl. No.: 10/316,989

(22) Filed: Dec. 10, 2002

(65) Prior Publication Data

US 2003/0228644 A1 Dec. 11, 2003

Related U.S. Application Data

(63) Continuation of application No. PCT/US01/18869, filed on Jun. 12, 2001, now abandoned.

(60) Provisional application No. 60/211,036, filed on Jun. 12, 2000.

(51) Int. Cl.
*C07C 229/00* (2006.01)

(52) U.S. Cl. .................. 562/433; 562/440; 562/457; 564/192; 564/180; 564/315

(58) Field of Classification Search ............ 558/70, 558/190, 181; 562/8, 11; 546/22
See application file for complete search history.

(56) References Cited

U.S. PATENT DOCUMENTS

| | | | |
|---|---|---|---|
| 2,829,148 A | 4/1958 | Chalkley | 260/391 |
| 2,839,542 A | 6/1958 | Chalkley | 260/391 |
| 2,839,543 A | 6/1958 | Chalkley | 260/394 |
| 2,855,303 A | 10/1958 | Chalkley | 96/90 |
| 2,936,235 A | 5/1960 | Chalkley | 96/85 |
| 3,798,131 A | 3/1974 | Rounds et al. | 435/6 |
| 4,399,131 A | 8/1983 | Durckheimer | 424/246 |
| 4,599,303 A | 7/1986 | Yabusaki et al. | 935/78 |
| 4,626,501 A | 12/1986 | Landes | 435/6 |
| 4,656,127 A | 4/1987 | Mundy | 435/6 |
| 4,683,194 A | 7/1987 | Saiki et al. | 435/6 |
| 4,716,106 A | 12/1987 | Chiswell | 435/5 |
| 5,428,163 A | 6/1995 | Mills | 544/732 |

FOREIGN PATENT DOCUMENTS

| | | |
|---|---|---|
| EP | 078636 | 6/1985 |
| WO | WO 01/95944 | * 12/2001 |

OTHER PUBLICATIONS

CA:113:184733 abs of WO 8909833 Oct. 1989.*
CA:123:296612 abs of US 5428163 Jun. 1995.*
CA:125:67247 abs of JP08073338 Mar. 1996.*
Downing, D.T., et al., Biochem. Biophys. Research Comm., 40, 218-223 (1970).
Dreyer, J.F., "Self-Attenuating Opthalmic Filter", Report WADD-TR-60-632, Feb. 1961, AD 322820.
Dreyer, J.F., et al., "Investigation of Materials and Systems for Protection Against Flash Blindness Effects of Nuclear Detonations," Report 68-38-CM, AD 688692 (1982).
Dreyer, J.F., Polacoat Inc., Tech. Report SEG-TR-65-50, 1-40, Oct. 1965.
Dreyer, J.F., Polacoat Inc., WADD Tech. Report 60-827, Contract AF 33(616)-6715,Feb. 1-20, 1961.
Tunnicliff, G., et al. Experientia, 33, 20-22 (1977).

* cited by examiner

*Primary Examiner*—Johann Richter
*Assistant Examiner*—Karl Puttlitz
(74) *Attorney, Agent, or Firm*—Lahive & Cockfield, LLP.; Giulio A. DeConti, Jr.; Jacob G. Weintraub

(57) ABSTRACT

Prodrug compounds capable of permeating a desired biological compartment and releasing a biologically active molecule in active form to effect a therapeutic functional change in the compartment to which it is introduced.

21 Claims, No Drawings

PRO DRUGS FOR SELECTIVE DRUG DELIVERY

RELATED APPLICATIONS

This application is a continuation of International Application No. PCT/US01/18869, filed Jun. 12, 2001, now abandoned, which claims the benefit of Provisional Application No. 60/211,036, filed Jun. 12, 2000, now abandoned.

BACKGROUND OF THE INVENTION

The effects of the preponderance of drugs result from their interaction with functional macromolecular components of the organism. Such interaction alters the function of the pertinent cellular component and thereby initiates the series of biochemical and physiological changes that are characteristic of the response to the drug. The term "receptor" denotes the component of the organism with which the chemical agent interacts. There are fundamental corollaries to the statement that the receptor for a drug can be any functional macromolecular component of the organism. One is that a drug is potentially capable of altering the rate at which any bodily function proceeds; a second is that, by virtue of interactions with specific receptors, drugs do not create effects but merely modulate the rates of ongoing functions. A simple pharmacological dictum thus states that a drug cannot impart a new function to a cell. Functional changes due to a drug result from either enhancement or inhibition of the unperturbed rate. Furthermore, a drug that has no direct action can cause a functional change by competition for a binding site with another, active regulatory ligand of the receptor. Drugs are termed agonists when they cause effects as a result of direct alteration of the fundamental properties of the receptor with which they interact. Compounds that are themselves devoid of intrinsic pharmacological activity, but cause effects by inhibition of the action of a specific agonist (e.g. by competition for agonist binding sites) are designated as antagonists.

At least from a numerical standpoint, the proteins of the cell form the most important class of drug receptors. Examples include the enzymes of crucial metabolic or regulatory pathways (e.g., tyrosine hydroxylase; 3-hydroxy-3-methylglutaryl-CoA reductase). Of equal interest are proteins involved in transport processes (e.g. $Ca^{2+}$-ATPase; $Na^+$-$K^+$-ATPase) or those that are protein kinases which activate other proteins as a consequence of their binding a secondary messenger such as cAMP. Specific binding properties of other cellular constituents can be exploited. Thus, nucleic acids are important drug receptors, particularly for chemotherapeutic approaches to the control of malignancy, and plant lectins shown remarkable specificity for recognition of specific carbohydrate residues in polysaccharides and glycoproteins. Small ions such as $Ca^{2+}$ which can function as a regulatory ion or $Fe^{2+}$ which can serve as an essential enzymatic cofactor can be exploited as drug receptors. And, drugs can also produce a functional change by a nonreceptor-mediated action. Certain drugs that are structural analogues of normal biological constituents may be incorporated into cellular components and thereby alter their function. This has been termed a "counterfeit incorporation mechanism" and has been implemented with analogues of purines and pyrimidines that can be incorporated into nucleic acids and that have utility in cancer chemotherapy and that have antiviral activity. Also, specific constituents of pathogens can be exploited as receptors. For example, the electron carriers of bacteria can serve as receptors as described U.S. application Ser. No. 948,326, which is incorporated herein by reference, and the replicative enzymes of viruses can be serve as receptors for the virus HIV. Many compounds are known which have receptor or nonreceptor mediated in vitro activity as appears in *The Handbook of Enzyme Inhibitors,* Mahendra Kumor Jain, 1982, Wiley Interscience, New York, incorporated herein by reference. However, only a small percentage produce the desired functional change in vivo or have a high therapeutic ratio, because they are toxic in their free form; they are rapidly inactivated or excreted; or, they cannot obtain access to their target receptor or site of action because they are impermeant to cells or biological barriers such as the blood brain barrier due to unfavorable energetics due, for example, to the possession of polar or charge groups; or, they are toxic as a consequence of being nonselective with regards to their access to and action with receptors in one biological environment or compartment relative to another. In these cases, compounds which demonstrate in vitro efficacy are ineffective therapeutics.

SUMMARY OF THE INVENTION

The present disclosure relates to chemical compositions and methods for delivering biologically active agents to a biological compartment. In an embodiment, the invention relates to a chemical compound having the formula A-B, where A is a moiety capable of receiving energy and B is a biologically active agent covalently bonded to B, wherein the bond between A and B is capable of heterolytic cleavage upon reception of energy by A.

In an advantageous embodiment, the energy causes A to achieve an excited state, the relaxation of which causes heterolytic cleavage of the bond between A and B. In another embodiment, A is a photochromic or thermochromic moiety. In yet another embodiment, the chemical compound is 1-phosphonoformate,1,5-di-(p-N-ethyl-N-ethylaminophenyl)-1,5-bis-(p-N,N-dimethylaniline)-1,3-pentadiene.

The invention also pertains to a method for selectively delivering a biologically active agent to a biological compartment, which comprises introducing a chemical compound having the formula A-B, where A is a carrier moiety and B is the biologically active agent, into a biological compartment and exposing the chemical compound to an energy sufficient to cause heterolytic cleavage of the bond between A and B, thereby releasing B from A.

DETAILED DESCRIPTION OF THE INVENTION

The invention relates to a chemical compound having the formula A-B, where A is a moiety capable of receiving energy and B is a biologically active agent covalently bonded to B, wherein the bond between A and B is capable of heterolytic cleavage upon reception of energy by A.

In a preferred embodiment, the chemical compound is a prodrug, e.g., that permeates the desired biological compartment and undergoes release of a biologically active agent, in an active form, inside of the desired compartment. In a further embodiment, the prodrug achieves a greater therapeutic effect or therapeutic ratio relative to the free drug alone as a consequence of altered pharmacokinetics or pharmacodynamics (such as a desirable kinetics of release, a resistance to inactivation or excretion, greater solubility, enhanced absorption, a diminished toxicity, or greater access to the cellular or biological compartment which is the site of action of the drug).

In an advantageous embodiment, A is a photochromic or thermochromic molecule, and B is a biologically active agent such as a drug moiety. In yet another embodiment, A comprises a cationic dye which demonstrates photochromic behavior with electromagnetic radiation and bleaching agents. Some examples of cationic dyes which can be used for A are di or triarylmethane dyes, triarylmethane lactone or cyclic ether dyes, cationic indoles, pyronines, phthaleins, oxazines, thiazines, acridines, phenazines, anthocyanidins, cationic polymethine dyes, azo or diazopolymethines, styryls, cyanines, hemicyanines, and dialkylaminopolyenes.

In a preferred embodiment, the chemical compound is a luminide. A luminide comprises a universal carrier molecule linked to one or more of virtually any biologically active agent including known pharmaceuticals and pesticides. The luminide conjugate potentiates delivery to the desired biological compartment and potentiates intracellular uptake of the biologically active agent which breaks apart due to a reversible bond between the carrier moiety and the biologically active agent to result in release of the free biologically active agent, allowing the desired pharmacological effect to occur. An embodiment of a luminide is a cellular permeant prodrug where intracellular drug release occurs when the prodrug undergoes heterolytic cleavage of the bond between a drug moiety and a carrier moiety. In another embodiment, the luminide is a two-part molecule where each part is a functionality with a defined purpose.

An exemplary luminide is of the structure A-B, where A represents a functionality which forms a reversible bond with B, which is released through heterolytic cleavage of the covalent bond of A with B. B is, in an embodiment, a drug moiety which is released in its free form into the environment. The free drug moiety effects a therapeutic functional change in the system to which it is introduced. Such mechanisms may include receptor mediated mechanisms including reversible and irreversible competitive agonism or antagonism, e.g., a molecule known as a "suicide substrate", a transition state analogue, or a noncompetitive or uncompetitive agonism or antagonism, or the mechanism may be a nonreceptor mediated mechanism such as a "counterfeit incorporation mechanism". The heterolytic cleavage releases the drug moiety into the desired compartment in active form to effect a greater therapeutic effect or therapeutic ratio relative to the free drug moiety alone as a consequence of altered pharmacokinetics or pharmacodynamics such as a desirable kinetics of release, a resistance to inactivation or excretion, greater solubility, enhanced absorption, a diminished toxicity, or greater access to the cellular or biological compartment which is the site of action of the drug moiety. In an embodiment, the B moiety is a bleaching agent (a molecule which covalently bonds to A, the carrier moiety of the Luminide such as a photochromic functionality). Such agents comprise essentially any nucleophilic group including phosphate, sulfide, sulfite, sulfate, carboxylate, hydroxyl, or amine.

The invention also pertains to a method for selectively delivering a biologically active agent to a biological compartment, which comprises introducing a chemical compound having the formula A-B, where A is a carrier moiety and B is the biologically active agent, into a biological compartment and exposing the chemical compound to an energy sufficient to cause heterolytic cleavage of the bond between A and B, thereby releasing B from A.

In another embodiment, effective drug delivery is achieved based on the stability of the A-B reversible bond which has a sufficient stability (i.e., a long enough half-life) to permit the prodrug to penetrate the desired biological compartment before the drug moiety is released through heterolytic cleavage of the A-B bond. In another embodiment, the mechanism of drug delivery comprises a dynamic equilibrium between B (drug moiety) bound and unbound to A (carrier moiety). The dynamic equilibrium of the carrier moiety and drug moiety to form the prodrug is:

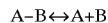

The prodrug penetrates the desired biological compartment wherein the release occurs. The drug moiety may become trapped inside the desired biological compartment. Thus, the concentration of drug moiety increases over time due to the dynamic transport by the carrier moiety which forms a labile product with the drug moiety.

A luminide may comprise a hybrid molecule of a specified biologically active agent having the optimal structure to achieve the highest therapeutic ratio and a carrier which is modified to achieve optimal bioavailability for a given drug. Thus, the physicochemical properties of a prodrug which change its bioavailability can be manipulated without altering the optimal drug structure. Luminide technology is applicable to essentially all biologically active agents. Luminides may used in any one of the following uses: antilipidemic drugs, anticholesterol drugs, aontraceptive agents, anticoagulants, anti-inflammatory agents, immunosuppressive agents, antiarrhythmic agents, antineoplastic drugs, antihypertensive drugs, epinephrine blocking agents, cardiac inotropic drugs, antidepressant drugs, diuretics, antifungal agents, antibacterial agents, anxiolytic agents, sedatives, muscle relaxants, anticonvulsants, agents for the treatment of ulcer disease, agents for the treatment of asthma and hypersensitivity reactions, antithromboembolytic agents, agents for the treatment of muscular dystrophy, agents to effect a therapeutic abortion, agents for the treatment of anemia, agents to improve allograft survival, agents for the treatment of disorders of purine metabolism, agents for the treatment of ischemic heart disease, agents for the treatment of opiate withdrawal, agents which activate the effects of secondary messengers, including inositol triphosphate, agents to block spinal reflexes, antiviral agents (including agents for the treatment of AIDS), pesticide applications, herbicide applications, and veterinary applications.

In an embodiment, the A moiety may be a photochromic or thermochromic molecule, e.g., the A moieties described in Table II of U.S. Pat. No. 5,773,592. An exemplary A moiety is a polymethine dye or triarylmethane dye covalently bound to B. The B moiety may be any biologically active agent which covalently binds to the A moiety (e.g., as a bleaching reaction,) and wherein the bond between A and B is reversible such that the heterolytic cleavage of the covalent bond between A and B may occur inside of the desired biological compartment such as an intracellular compartment, thereby releasing B. Exemplary B moieties are shown in Table 2 herein. Phosphonoformate (Foscarnet), an HIV-reverse transcriptase inhibitor, is an exemplary B moiety. Exemplary B moieties can also be found in Table 3 and the References at column 161 to 170 of U.S. Pat. No. 5,773,592.

Some examples of B moieties that are antihypertensive agents are tyrosine hydroxylase inhibitors such as 3,5-diiodo-4-hydrobenzoic acid; dopamine B-hydroxylase inhibitors such as mimosine and 2-mercaptoethylamine; dopa decarboxylase inhibitors such as D,L-hydrazino-α-methyldopa; and histindine decarboxylation inhibitors such as NSD 1055.

Some examples of B moieties that may be either sedatives, muscle relaxants, or anticonvulsants are neurotransmitters such as γ-aminobutyric acid; 2-oxoglutarate aminotransferase inhibitors such as gabaculine and N-(5'-phosphopyridoxyl-4-aminobutyric acid; GABA release enhancers such as baclofen; and GABA uptake inhibitors such as trans-4-aminocrotonic acid. Some examples of B moieties that are anxoilytics are 2-oxoglutarate aminotransferase inhibitors such as gabaculine and N-(5'-phosphopyridoxyl-4-aminobutyric acid; GABA release enhancers such as baclofen; and GABA uptake inhibitors such as trans-4-aminocrotonic acid.

Some examples of B moieties that are anticholesterol agents are HMG-CoA reductase inhibitors such as compactin and 3-hydroxy-3methylglutarate. Some examples of B moieties that are antifungal agents are class II aldolase inhibitors such as p-glycolohydroxomate and chitin synthetase inhibitors such as polyoxin D. An example of a B moiety that is an antibacterial agent is p-glycolohydroxomate, a class II aldolase inhibitor. An example of a B moiety that is an antineoplastic agent is the aspartate transcarbamylase inhibitor N-(phosphonacetyl)-L-asparatate.

An exemplary A moiety is 1,5-di-(p-N-ethyl-N-ethylaminophenyl)-1,5-bis-(p-N,N-dimethylaniline)-1,3-pentadiene or the related reactive perchlorate salt, 4-[1,5-Bis-(4-diethylamino-phenyl)-5-(4-dimethylamino-phenyl)-penta-2,4-dienylidene]-cyclohexa-2,5-dienylidene-ammonium perchlorate, which is shown in Table 1.

TABLE 1

Exemplary A Moiety

| Name | Structure |
|---|---|
| 4-[1,5-Bis-(4-diethylamino-phenyl)-5-(4-dimethylamino-phenyl)-penta-2,4-dienylidene]-cyclohexa-2,5-dienylidene-ammonium perchlorate | 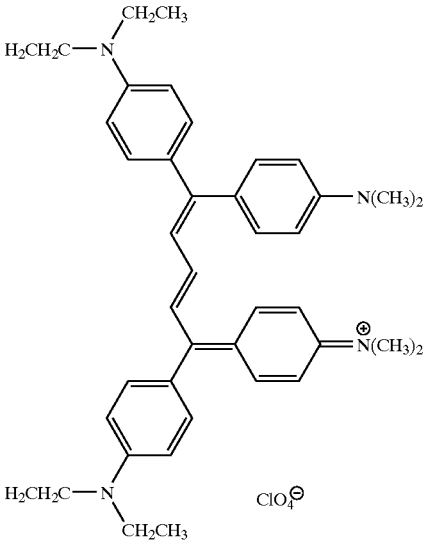 |

TABLE 2

Exemplary B Moieties

| Name | Structure |
|---|---|
| phosphonoformate | 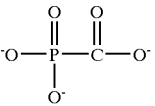 |
| 3,5-diiodo-4-hydrobenzoic acid | 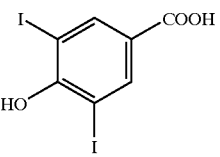 |
| γ-aminobutyric acid | $H_2NCH_2CH_2CH_2COOH$ |

TABLE 2-continued

Exemplary B Moieties

| Name | Structure |
|---|---|
| gabaculine | cyclohexadiene with COOH and NH$_2$ substituents |
| N-(5'-phosphopyridoxyl)-4-aminobutyric acid | pyridine ring with CH$_2$OP(=O)(OH)OH, CH$_2$NHCH$_2$CH$_2$CH$_2$COOH, OH, and H$_3$C substituents |
| baclofen | 4-chlorophenyl-CH(CH$_2$NH$_2$)CH$_2$COOH |
| trans-4-aminocrotonic acid | H$_2$NCH$_2$CH=CHCOOH |
| compactin | (structure shown) |
| 3-hydroxy-3-methylglutarate | CH$_3$CH$_2$C(OH)(CH$_3$)CH$_2$COOH |
| P-glycolohydraoxamate | $^-$O-P(=O)(O$^-$)-O-CH$_2$-C(O$^-$)=N-OH |

TABLE 2-continued

Exemplary B Moieties

| Name | Structure |
|---|---|
| N-(phosphonacetyl)-1-aspartate | (structure) |
| phosphonoacetate | (structure) |
| mimosine | (structure) |
| 2-mercaptoethylamine | $HSCH_2CH_2NH_3^+$ |
| NSD 1055 | (structure) |
| polyoxin D | (structure) |
| D,L-hydrazino-α-methyldopa | (structure) |

An exemplary luminide, i.e., A-B compound, is 1-phosphonoformate,1,5-di-(p-N-ethyl-N-ethylaminophenyl)-1,5-bis-(p-N,N-dimethylaniline)-1,3-pentadiene shown in Table 3.

TABLE 3

| Name | Structure |
|---|---|
| 1-phosphonoformate,1,5-di-(p-N-ethyl-N-ethylaminophenyl)-1,5-bis-(p-N,N-dimethylaniline)-1,3-pentadiene | (structure) |

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A chemical compound having the formula A-B, where A is a moiety capable of receiving energy, wherein A is 1,5-di-(p-N-ethyl-N-ethylaminophenyl)-1,5-bis-(p-N,N-dimethylaniline)-1,3-pentadiene; and B is a biologically active agent covalently bonded to A, wherein B is selected from the group consisting of N-(5'-phosphopyridoxyl)-4-aminobutyric acid, p-glycolohydroxamate, N-(phosphonoacetyl)-L-aspartate, phosphonoacetate, and phosphonoformate, wherein the bond between A and B is capable of heterolytic cleavage upon reception of energy by A.

2. The chemical compound of claim 1, wherein said energy causes A to achieve an excited state; and relaxation of said excited state of A causes heterolytic cleavage of said covalent bond between A and B.

3. The chemical compound of claim 1, wherein said chemical compound is 1-phosphonoformate, 1,5-di-(p-N-ethyl-N-ethylaminophenyl)-1,5-bis-(p-N,N-dimethylaniline)-1,3-pentadiene.

4. The chemical compound of claim 1, wherein B is phosphonoacetate or phosphonoformate.

5. The chemical compound of claim 1, wherein B is N-(5'-phosphopyridoxyl)-4-aminobutyric acid.

6. The chemical compound of claim 1, wherein B is selected from the group consisting of p-glycolohydroxamate.

7. The chemical compound of claim 1, wherein B is N-(phosphonoacetyl)-L-aspartate.

8. A method for selectively delivering a biologically active agent to a biological compartment, which comprises: introducing a chemical compound having the formula A-B, where A is a carrier moiety, wherein A is 1,5-di-(p-N-ethyl-N-ethylaminophenyl)-1,5-bis-(p-N,N-dimethylaniline)-1,3-pentadiene, and B is a biologically active agent, wherein B is selected from the group consisting of N-(5'-phosphopyridoxyl)-4-aminobutyric acid, p-glycolohydroxamate, N-(phosphonoacetyl)-L-aspartate, phosphonoacetate, and phosphonoformate, into said biological compartment; and exposing said chemical compound to an energy sufficient to cause heterolytic cleavage of said bond between A and B, thereby releasing B from A.

9. The method of claim 8, wherein said energy causes A to achieve an excited state; and relaxation of said excited state of A causes heterolytic cleavage of said covalent bond between A and B.

10. The method of claim 8, wherein said chemical compound is 1-phosphonoformate,1,5-di-(p-N-ethyl-N-ethylaminophenyl)-1,5-bis-(p-N,N-dimethylaniline)-1,3-pentadiene.

11. The method of claim 8, wherein B is phosphonoformate.

12. The method of claim 8, wherein B is selected from the group consisting of phosphonoacetate and phosphonoformate.

13. The method of claim 12, wherein B is an antiviral agent.

14. The method of claim 8, wherein B is N-(5'-phosphopyridoxyl)-4-aminobutyric acid.

15. The method of claim 14, wherein B is an anticonvulsant.

16. The method of claim 8, wherein B is p-glycolohydroxamate.

17. The method of claim 16, wherein B is an antibacterial or antifungal agent.

18. The method of claim 8, wherein B is N-(phosphonoacetyl)-L-aspartate.

19. The method of claim 18, wherein B is an antineoplastic agent.

20. The method of claim 8, wherein said energy is electromagnetic radiation.

21. The method of claim 8, wherein said energy is heat energy.

* * * * *